US009289120B2

(12) United States Patent
Rajan et al.

(10) Patent No.: US 9,289,120 B2
(45) Date of Patent: Mar. 22, 2016

(54) TEMPORAL STRUCTURED-ILLUMINATION MOTION-DETECTION SYSTEM

(71) Applicant: Massachusetts Institute of Technology, Cambridge, MA (US)

(72) Inventors: Nandini Rajan, Lincoln, MA (US); Andrew M. Siegel, Arlington, MA (US)

(73) Assignee: Massachussetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/413,306

(22) PCT Filed: Mar. 12, 2013

(86) PCT No.: PCT/US2013/030441
§ 371 (c)(1),
(2) Date: Jan. 7, 2015

(87) PCT Pub. No.: WO2014/018102
PCT Pub. Date: Jan. 30, 2014

(65) Prior Publication Data
US 2015/0190051 A1    Jul. 9, 2015

Related U.S. Application Data

(60) Provisional application No. 61/675,481, filed on Jul. 25, 2012.

(51) Int. Cl.
*A61B 3/02* (2006.01)
*A61B 3/113* (2006.01)
*G06T 7/20* (2006.01)
*G06K 9/00* (2006.01)
*A61B 3/00* (2006.01)
*A61B 3/14* (2006.01)
*A61B 5/11* (2006.01)

(52) U.S. Cl.
CPC .............. *A61B 3/113* (2013.01); *A61B 3/0025* (2013.01); *A61B 3/14* (2013.01); *G06K 9/00604* (2013.01);*G06T 7/204* (2013.01); *G06T 7/2033* (2013.01); *A61B 5/1128* (2013.01); *G06T 2207/10152* (2013.01); *G06T 2207/30041* (2013.01)

(58) Field of Classification Search
CPC ................................. G06F 3/013; A61B 3/10
USPC .......... 351/224, 225, 223, 222, 246; 345/157, 345/156, 158
See application file for complete search history.

(56) References Cited

U.S. PATENT DOCUMENTS 5,094,521 A * 3/1992 Jolson .................... A61B 3/085
351/206
5,302,981 A * 4/1994 Wirtz ....................... A61B 3/08
351/222

(Continued)

OTHER PUBLICATIONS

International Search Report completed Jun. 13, 2013 for International Application No. PCT/US2013/030441 entitled "Temporal Structured-Illumination Motion-Detection System" filed Mar. 12, 2013.

(Continued)

*Primary Examiner* — Hung Dang
(74) *Attorney, Agent, or Firm* — Hamilton, Brook, Smith & Reynolds, P.C.

(57) ABSTRACT

The present invention provides devices and methods for detecting and tracking fast-moving-object. In one application, the present invention can be employed to detect and track fast eye movements (saccades). An example device of the present invention tracks a moving object by generating, within a single frame of a detector (e.g., a video camera) two or more images of the moving object. The images are generated by illuminating the moving objects with sequentially activated light sources (e.g. sequentially strobed light-emitting diodes). The rate at which the light sources are sequentially activated exceeds the frame rate of the detector, resulting in generating multiple images of the moving object within a single frame of the detector. The devices and methods described herein, including a saccadometry system, can utilize off-the-shelf components and does not require expensive high-frame-rate video equipment. These devices and methods can be used to track a moving object with a temporal resolution far greater than that normally achievable with standard 15 fps to 30 fps frame-rate imagers.

28 Claims, 11 Drawing Sheets

(56) References Cited

U.S. PATENT DOCUMENTS

| | | | |
|---|---|---|---|
| 5,343,261 A * | 8/1994 | Wilson | A61H 5/00 351/203 |
| 2009/0174701 A1 | 7/2009 | Cotter et al. | |
| 2011/0069199 A1 | 3/2011 | Yamazaki | |

OTHER PUBLICATIONS

PCT/US2013/030441 Notification Concerning Transmittal of International Preliminary Report on Patentability dated Feb. 5, 2015 entitled "Temporal Structured-Illumination Motion-Detection System.".

* cited by examiner

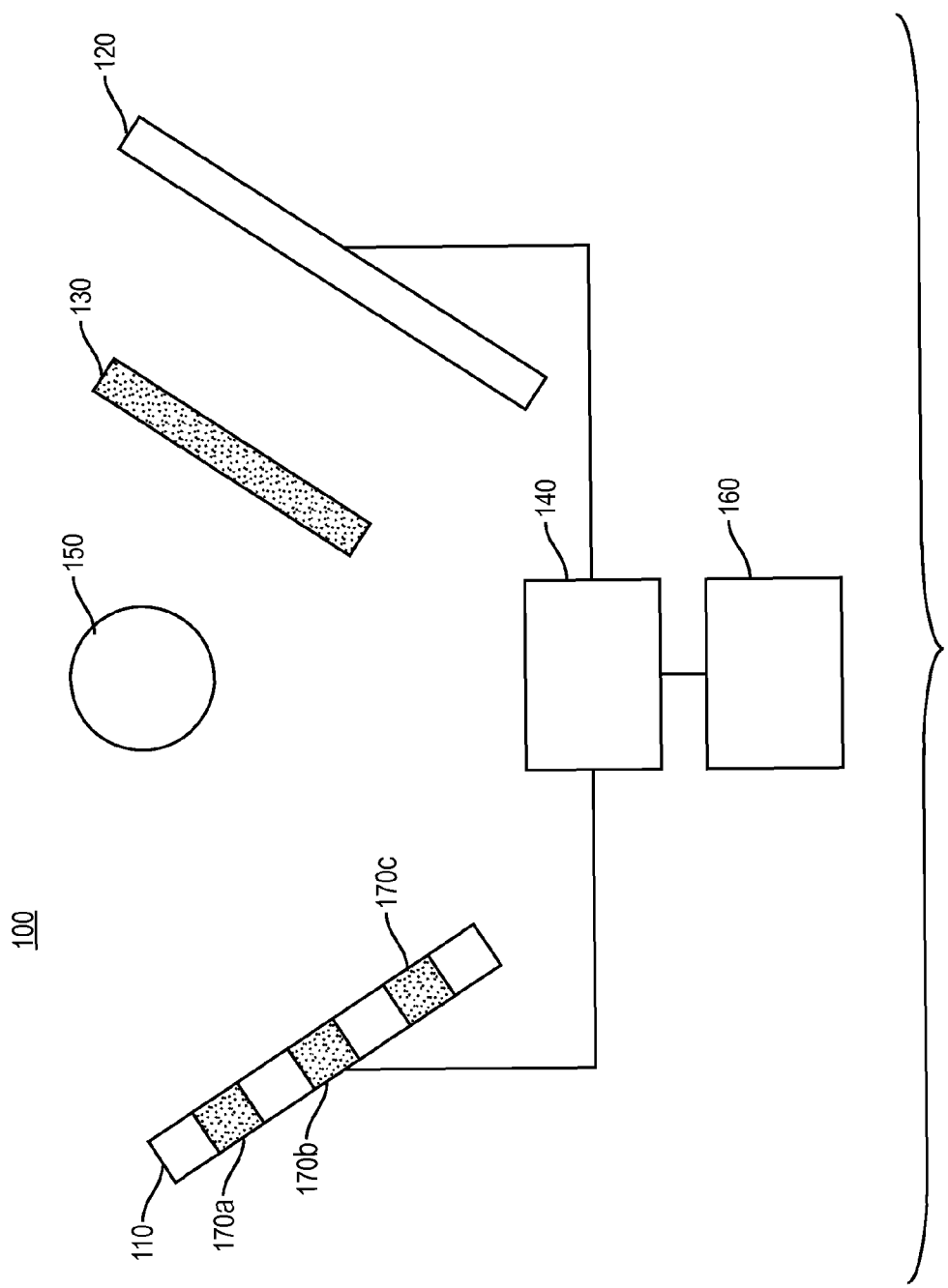

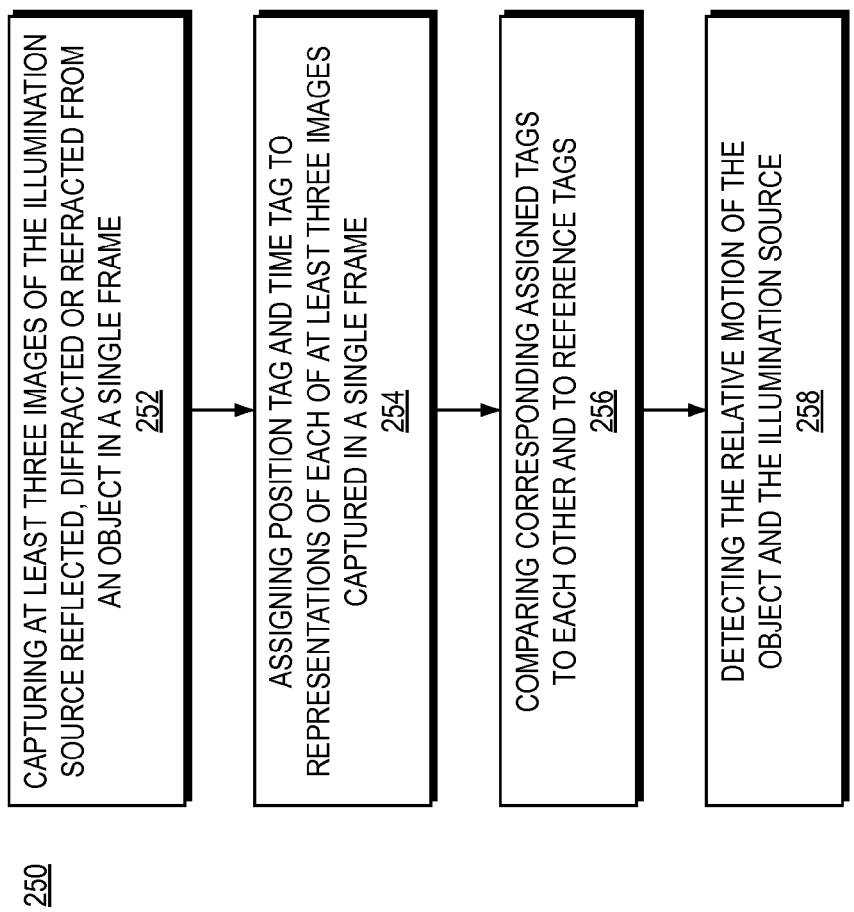

TEMPORAL STRUCTURED-ILLUMINATION MOTION-DETECTION SYSTEM

RELATED APPLICATION(S)

This application is the U.S. National Stage of International Application No. PCT/US2013/030441, filed Mar. 12, 2013, which designates the U.S., published in English, and claims the benefit of U.S. Provisional Application No. 61/675,481, filed on Jul. 25, 2012. The entire teachings of the above application(s) are incorporated herein by reference.

GOVERNMENT SUPPORT

This invention was made with government support under MIT Lincoln Laboratory Allocated Biomedical Program IR40-012 awarded by the U.S. Air Force. The government has certain rights in the invention.

BACKGROUND OF THE INVENTION

Numerous technologies and processes require tracking rapidly moving objects. An example of such application is saccadometry, tracking and measuring rapid eye movements. Saccadometry is important, in particular, as a tool for monitoring health conditions that influence the saccadic motion of the eyes. Saccadometry requires temporal sampling of eye position at rates of 300 Hz or greater in order to detect these rapid changes in gaze.

Traditionally, saccadometry relies on fast-framing imagers of some type to solve this temporal sampling rate problem. Existing eye tracker systems acquire high format, high speed video (500-1500 fps), some utilizing IR light reflection from the pupil. They tend to be expensive (on the order of $45,000 USD and higher at today's prices), cumbersome (due to head-mounts/restraints and accompanying hardware), and have large data storage requirements making it unlikely to be deployed in the field. Saccadometers are typically less expensive ($20,000-35,000 USD), but can record only horizontal eye movements, and require both IR and laser sources. In addition, existing saccadometers provide only an average cyclopean position of the two eyes in the horizontal plane. These are specialized systems used for medical research and diagnostics. Sophisticated tracking software is required to extract saccade information from full frame imagery.

SUMMARY OF THE INVENTION

An embodiment of the present invention provides for a fast-moving-object detection and tracking system, including a saccadometry system that can utilize off-the-shelf components and does not require high-frame-rate video equipment.

Accordingly, one example embodiment of the present invention is a device that comprises a detector, a focusing element, and an illumination source. The detector is configured to capture frames according to a frame acquisition time. The illumination source is configured, in cooperation with the focusing element and the detector, to generate at least first and second images of the illumination source on the detector within a given frame. During the operation of the device, the first image and the second image are generated in a temporal sequence and form a spatial sequence on the focal plane of the detector. The first and the second images are spatially separated from each other on the focal plane of the detector by at least one pixel. The illumination source has a time delay between generating the first image and the second image. The time delay is less than or equal to the frame acquisition time of the detector.

Another example embodiment of the present invention is a method of detecting relative motion of an object and an illumination source. A position tag and a time tag are assigned to representation of each of at least three spatially distinct images of the illumination source captured in a spatial sequence and a temporal sequence in a first frame. The corresponding position tags and time tags are compared to each other and to reference position tags and reference time tags. Relative motion of the object and the illumination source is then detected based on the comparing.

In another example embodiment of the present invention is a method of detecting saccades in a subject. At least a first image and a second image of a reflection of an illumination source in at least one eye of the subject are generated by the illumination source in cooperation with a focusing element. The first and second images are generated in a temporal sequence and are disposed on a focal plane of a detector in a spatial sequence. The detector has a frame acquisition time, the illumination source has a time delay between generating the first image and the second image, and the first image and the second image are spatially separated from each other on the focal plane of the detector by at least one pixel. The time delay of the illuminating source is less than or equal to the frame acquisition time of the detector.

Using the detector, the first and the second images are detected so that the first and the second images are detected within a given frame. The motion of the at least one eye is determined based on the spatial sequence and the temporal sequence of the first image and the second image.

Another example embodiment of the present invention is a method of detecting saccades in a subject. A position tag and a time tag are assigned to representations of each of at least three spatially distinct images of a reflection of an illumination source from an eye of the subject captured in a spatial sequence and a temporal sequence in a first frame of a detector. Corresponding position tags and time tags are compared to each other and to reference position tags and reference time tags. Saccades in the subject are detected based on the comparing.

The devices and methods described herein provide a number of advantages over the existing systems. For example, the methods and devices described herein can be constructed by using standard off-the-shelf components, such as LEDs, and standard frame-rate CCD or CMOS imagers. These devices and methods can be used to monitor the saccadic motion of the eye (or of any other reflecting surface, for example, a convex reflecting surface) with a temporal resolution far greater than that normally achievable with standard 15 fps to 30 fps frame-rate imagers. For example, if ten LEDs are used together with a 30 fps imager, then the temporal sampling of saccadic motion using the methods and devices described herein can approach 300 Hz (i.e. ten temporal samples per image frame).

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1B is a schematic diagram illustrating an example of a device described herein.

FIG. 2C is a flow diagram further illustrating the operation of an example method of the present invention.

DETAILED DESCRIPTION OF THE INVENTION

A description of example embodiments of the invention follows.

Figure 1A:
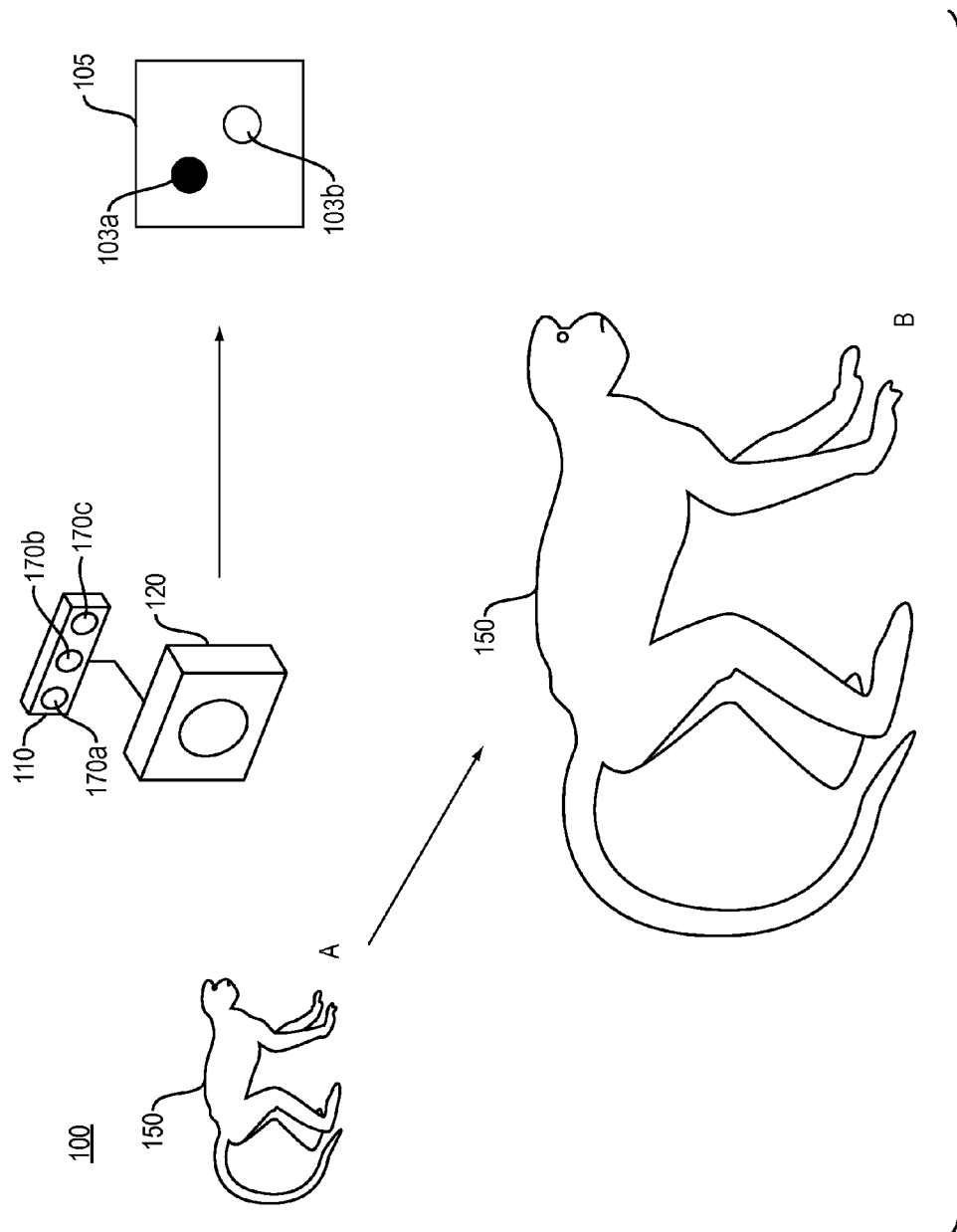
FIG. 1A is a schematic diagram illustrating the use of an example device of the present invention to detect a moving object.

An example embodiment of the present invention is device 100 shown in FIG. 1A. Device 100 includes detector 120 that captures at least a first and a second images 103*a* and 103*b* of object 150 within a single frame 105. Device 100 includes illumination source 110 configured to generate at least the first image 103*a* and the second image 103*b*.

Referring to FIG. 1B, device 100 includes illumination source 110, detector 120, and focusing element 130. Detector 120 is configured to capture frames according to a frame acquisition time. Illumination source 110 is configured, in cooperation with focusing element 130 and detector 120, to generate at least first and second images of illumination source 110 on the detector 120 within a given frame. Such images are shown in FIG. 2A as images 204 and 206 within frame 202 and in FIG. 2B as images 224 and 226 in frame 222.

Figure 2B:
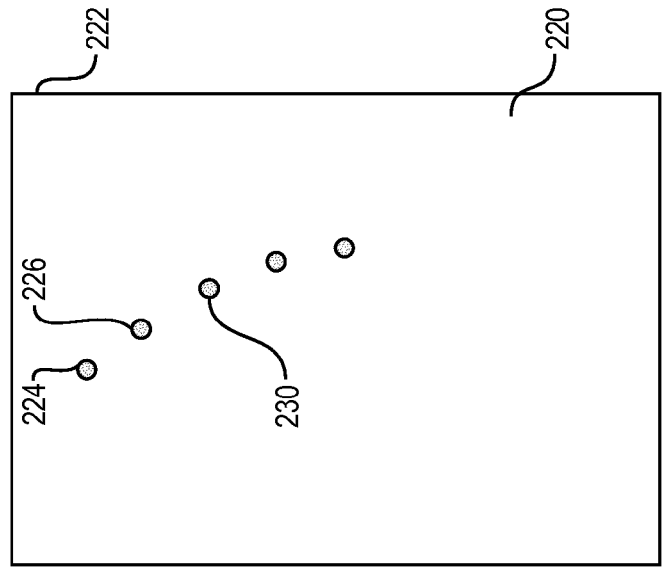
FIG. 2A and FIG. 2B are schematic diagram illustrating generation of images on a focal plane of a detector employed by devices described herein.
Figure 2A:
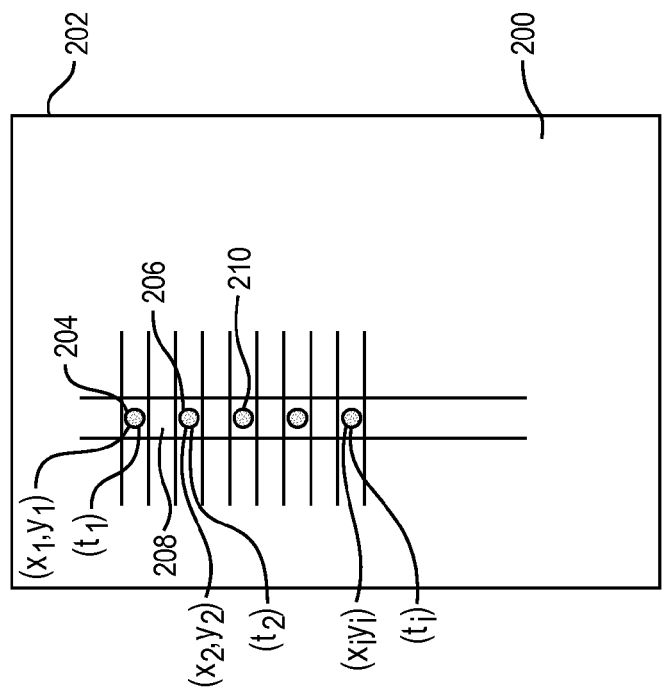

Referring to FIG. 2A, the first image 204 and the second image 206 form a spatial sequence and are spatially separated from each other on focal plane 200 of detector 120 by at least one pixel 208.

Because illumination source 110 has a time delay between generating the first image and the second image, the first and the second images 204 and 206 are generated in a temporal sequence. The time delay is less than or equal to the frame acquisition time of detector 120.

In one example, device 100 further includes processing module 140, configured to determine motion of object 150 relative to illumination source 110 based on the spatial sequence and the temporal sequence of the first image (204, 224) and the second image (206, 226).

In one example, device 100 further including transmitter 160 configured to transmit at least the first image (204, 224) and the second image (206, 226) to a remote storage site (not shown).

In certain example embodiments, illumination source 110 can be located on object 150. In other example embodiments of device 100 shown in FIG. 1, illumination source 110 can be configured to emit electromagnetic energy at the object causing the electromagnetic energy to reflect, refract or diffract from object 150 to detector 120.

In one example, detector 120, focusing element 130, and illumination source 110 can be integrated in a handheld device.

In certain example embodiments of device 100, illumination source 110 is further configured, in cooperation with focusing element 130 and detector 120, to generate a third image (210 in FIG. 2A, 230 in FIG. 2B) of illumination source 110 on detector 120 within the given frame (frame 202 in FIG. 2A, frame 222 in FIG. 2B). The first image, second image, and third image each being spatially separated from each other on the focal plane of the detector by at least one pixel, as shown in FIG. 2(A). Referring to FIG. 2A, in this example, illumination source 110 has a first time delay between generating the first image 204 and the second image 206, and a second time delay between generating the second image 206 and the third image 210. The first time delay and the second time delay are each less than or equal to the frame acquisition time of the detector.

In certain example embodiments, illumination source 110 includes at least two light emitters 170*a*, 170*b*, and 170*c*, shown in FIG. 1. For example, light emitters 170*a*, 170*b*, and 170*c* can form an array of sequentially activated light emitters. Light emitters 170*a*, 170*b*, and 170*c* can be activated in a sequence that is free-running, synchronous, or plesiochronous with respect to the detector.

As used herein, the terms "free-running," "synchronous," and "plesiochronous" refer to interrelationship between two or more cyclic events. "Free-running" is when both events (for example, the LED repetition rate and the camera frame rate) are completely independent of each other. Their rates could be very different from each other or very close to each other—but neither one is influenced by the other. "Synchronous" is when both events are coupled such that they both run at exactly the same rate, and with the same time relationship to each other. For example, the detector can be used to control the LED repetition rate such that each LED turns on and off at a specific time in each frame. "Plesiochronous" is when both events run at rates which are very close to, but not exactly the same as, each other. For example, the LED repetition rate can be very close to the detector frame rate.

In one example embodiment, illumination source 110 includes a single spatially modulated light emitter 170*a*. In this example, focusing element 130 can be an optical component within an optical train (not shown), such that light emitter 170*a* is spatially modulated by the optical train. In another example, light emitter 170*a* can be movable.

Another example of the present invention is a method of detecting relative motion of an object and an illumination source. Referring to FIG. 2A, to detect the relative motion, position tags $(x_1, y_1)$, $(x_2, y_2)$, and $(x_3, y_3)$ and time tags $(t_1)$, $(t_2)$, and $(t_3)$ are assigned to each of at least three spatially distinct images 204, 206, and 210, respectively, of the illumination source captured in a spatial sequence and a temporal sequence in a first frame 202 of focal plane 200 of detector 120. The assigned tags are then compared to each other as well as to reference position tags and reference time tags. As used herein, "comparing" the tag refers to numerically comparing and analyzing (a) the positional coordinates ($x_i$, $y_i$) of the captured images and the reference images, and (b) the values of time ($t_i$) assigned to each image. Based on this comparing, the relative motion of object 150 and illumination source 110 can be detected and measured.

In certain examples, the reference position tags and the reference time tags are based on prior knowledge of the positional sequence and the temporal sequence of the at least three images. In other examples, the reference position tags and the reference time tags are the position tags and time tags assigned to at least three images of the illumination source captured in a second frame. For example, images 204, 206, and 210 of frame 202 can serve as reference images for images 224, 226 and 230 of frame 222.

The operation of the above-described method is further explained with reference to the flow diagram depicted in FIG. 2C. The process 250 includes four operations. In operation 252, at least three images of the illumination source reflected, diffracted or refracted from an object are captured in a single frame. In operation 254, position tag and time tag to representations of each of at least three images captured in a single frame are assigned. In operation 254, corresponding assigned tags are compared to each other and to reference tags. In operation 258, the relative motion of the object and the illumination source are detected.

In certain examples, the methods described herein can be used to determine relative motion of not only object 150 of FIG. 1, but also at least one additional object (not shown) and illumination source 110.

In other examples, the devices and methods described herein can be used to compute an object's position as a function of time and the object's velocity as the function of time. In particular, the methods and devices described herein can be used to compute the object's angular velocity.

Another example embodiment of the present invention can be used to detect saccades. This example embodiment is a method of detecting saccades in a subject. In this example, referring to FIG. 1, object 150 can be an eye of a human or an animal. The devices and methods described herein can be used to detect the saccades along at least two axes. In other examples, the methods and devices described herein can be used to both distinguish large saccades from small saccades, and further, to quantify saccade magnitude and duration. Small versus large saccades can be distinguished based on both positional variance as well as duration. First, the motion axis is defined as the axis normal to the line defined by the images of at least two illumination sources. Next, positional variance is defined as the variance of the source image locations from their mean position along the motion axis in a single frame. Finally, saccade duration is defined as the number of frames in which the change in positional variance is greater than or equal to one pixel. Small saccades can be defined as the set of frames where positional variance per frame is less than or equal to one pixel and saccade duration is less than of equal to one frame. Large saccades can be defined as the set of consecutive frames such that positional variance per frame is greater than one pixel and saccade duration is greater than or equal to two frames. These criteria can be adjusted as needed, based upon the pixel angular subtense of the image sensor. A linear measure of saccade magnitude and duration is also available from the devices and methods described herein.

Either visible or infrared (IR) LEDs can be used, dependent on the spectral bandpass of the camera and the perception of the subject. The relatively low corneal irradiance minimizes distractions. No electrical connection is required between the illumination source and the imaging device. Simple user-adjustable timing combined with advanced image processing methods eliminates the need for absolute synchronization. The system requires no specialized head mount as derivable information from the imagery data allows for effective near real-time registration.

The devices and methods described herein can be employed in a number of applications.

For example, the devices and methods described herein can be used to capture high-speed saccade and microsaccades to assist in clinical diagnosis. Potential clinical applications include:

Ancillary or first phase assessment of such conditions as traumatic brain injury, concussion;
Psychiatric disorders such as ADD, autism assessment;
Dyslexia;
Multiple sclerosis,
Ocular palsies or flutters,
Brain lesions or tumors affecting vision or eye motion,
Sobriety assessment and compliance.

Further applications include the use of the devices and methods described herein in telemedicine. Examples include self-monitoring by the subjects with limited mobility or without accessibility to immediate medical care.

Further applications include the use of the devices and methods described herein in human-machine interfaces, for example, for eye tracking in video games, or for technologies enabling gestureless communication.

Further application of the devices and methods described herein is for low resolution mapping of corneal curvature via eye movement.

EXEMPLIFICATION

Example 1

Temporal Structured-Illumination Saccade System (TeSS)

Figure 3:
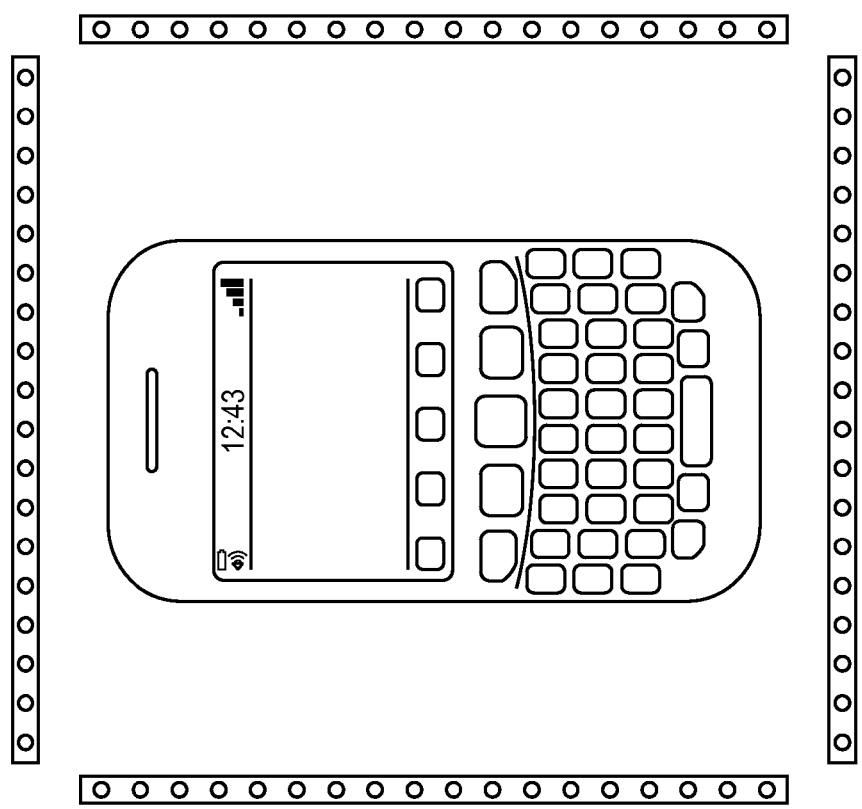
FIG. 3 is an illustration of a hand-held example of a device of the present invention that includes strobed light sources and a personal digital assistant (PDA) or cell phone containing a standard CCD or CMOS imager with a recording capability.
Figure 4:
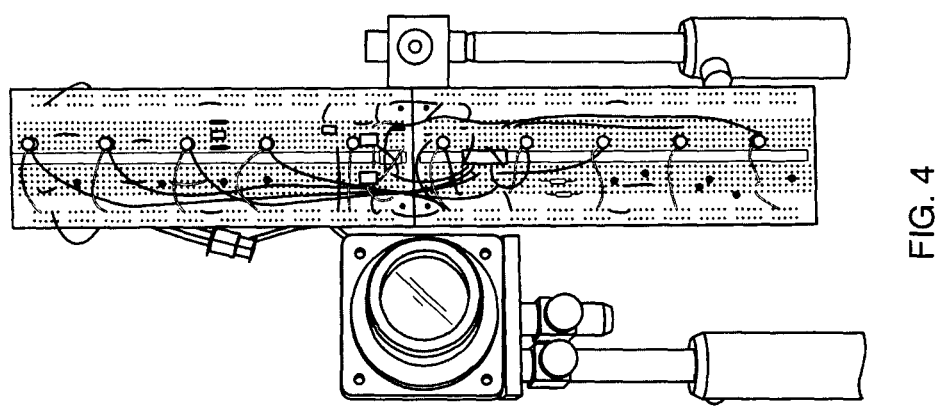
FIG. 4 is an illustration of an example embodiment of a device described herein.

A TeSS system was built using two hardware components: the strobed light sources and a PDA or cell phone containing a standard CCD or CMOS imager with a recording capability. One example of such a device is shown in FIG. 3. Another example, used in the experiments described below, is shown in FIG. 4. The TeSS system included a software component for image processing and strobe rate tuning. The software component includes a processing module that performs robust source image detection, identifies key eye features such as the pupil and iris to derive and estimate gaze direction, and a novel temporal deconvolution component that associates source image location with interframe time stamps. This derived per-frame spatial-time tag association, along with estimated gaze angle, is used to generate a time-varying scan of eye motion at a temporal resolution greater than the native frame-capture rate of the camera.

In this example, a linear, curved, or otherwise spatially defined pattern of discrete light sources generated a light signal that reflected off of a curved corneal surface of the eye to reach the imager. A linear array of ten LEDs separated far enough apart to create discrete points of light on the imager were used as an illumination source.

The LEDs were activated in a sequential, alternating, or otherwise temporally unique strobing sequence, generating a series of separate corneal reflections on the imager focal plane. In one example, a linear "1-of-n" strobe sequence, similar to the approach lighting system used at airport runways, was used. The spatial pattern in combination with the temporal sequencing of the light sources was designed so that the physical locations of the illuminated points on the imager contain both temporal and spatially encoded information concerning the motion of the eye.

Numerical methods designed to first deconvolve the temporal information encoded in each of the discrete image frames, and then to recombine the data from a sequence of image frames to construct a spatial time course for the eye position as a function of time were used. The process of deconvolving the temporally encoded information includes identifying the source image associated with the first illumination source that appears during the frame acquisition time. If the LED sequence and camera frame rate is synchronous, the first source image location is associated with the start of the LED sequence. If the LED sequence and camera rate is asynchronous or plesiochronous, the uncertain delay during camera capture and readout will lead to low intensity or missing source images. The first source image location during acquisition of a single frame, and thus the start or first time tag of the temporal sequence, will then be associated with the dimmest or missing source image location. Subsequent source images are then identified in a cyclic sequence, beginning from the first source image location, and are associated with consecutive interframe time tags.

The device shown in FIG. 4 was used to track eye movements of a human subject. During ocular motion, the temporally multiplexed LED image sequence reflected from the corneal surface and appeared spatially shifted in the resultant video image frame. The rate of ocular motion was directly correlated to the location and degree of the reflected source shift. The multiplicative improvement in temporal sampling was directly related to the number of LEDs along each axis. For example, if ten discrete LEDs were used, then the effective ocular sampling rate was ten times the camera frame rate.

Figure 5B:
FIG. 5A and FIG. 5B are photographs showing raw input image and a processed image of the reflections of strobed light emitters from a human eye. The pattern indicates a stationary eye.
Figure 5A:
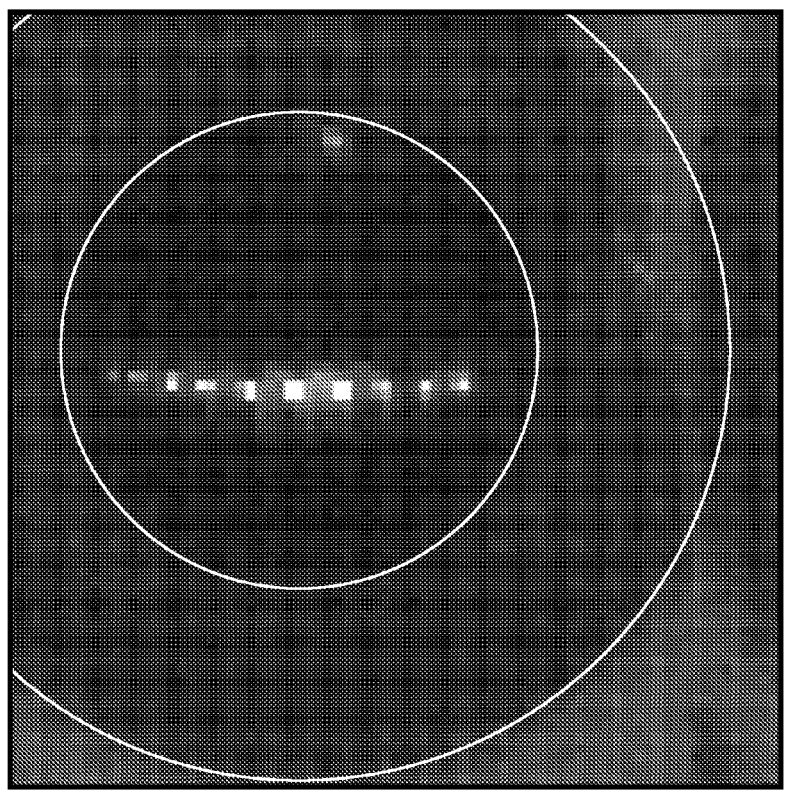

The system consisted of a video camera running at 15 fps to image an eye undergoing motion in the presence of temporal structured illumination. A sequence of ten LED sources were positioned linearly and cycled once during each frame, providing the equivalent of 150 fps sampling of eye motion, tagged in time by the LED source corneal reflectance position. FIG. 5A and FIG. 5B show the resultant output images for a stationary eye and one with multiple inter-frame saccades. Note the deviation from the almost linear pattern displayed in FIG. 5A that resulted from rapid eye movement, shown in FIG. 5B. This deviation is even more pronounced during larger eye motions as shown in FIG. 6.

Figure 6:
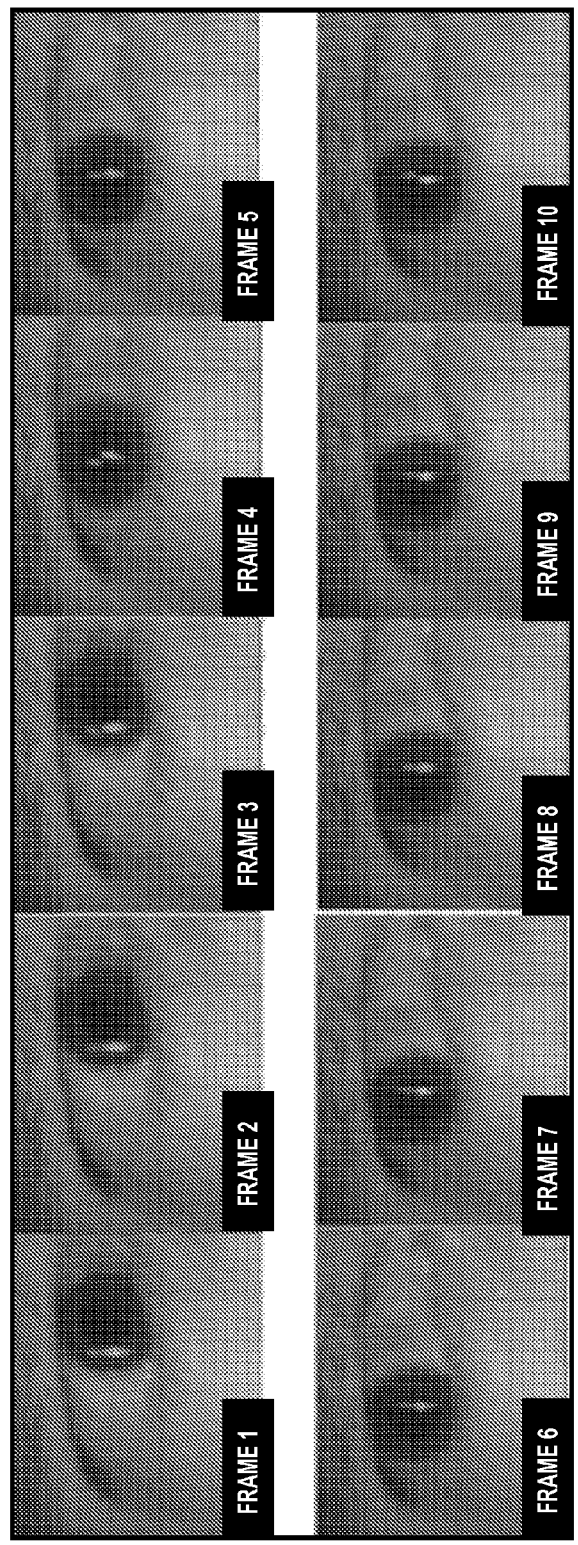
FIG. 6 is a series of photographs showing reflection of the strobed light emitters from a human eye during the eye movement.

In FIG. 6, large eye movements were tracked via spline fit of the corneal reflection distribution. Timing for initiation of large eye movements was possible at effective time samples much higher than collection video rates. In Frame 4 of FIG. 6, for instance, the start time for eye movement to the subject's right occured at approximately 0.02 seconds after the start time for acquiring the frame.

Figure 7C:
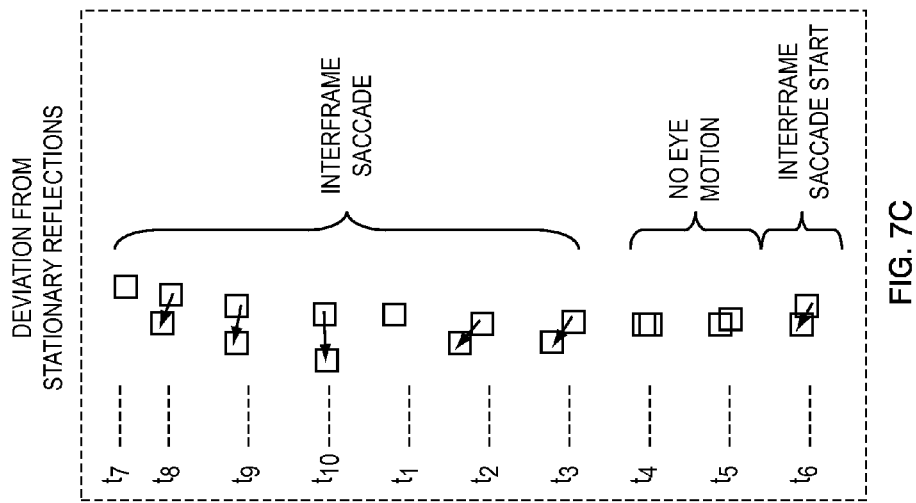
FIGS. 7A-7C are the photographs of strobed emitters reflecting from a human eye, representing raw input data (7A) and partially (7B) and fully processed image (7C). These photographs illustrate how the deviation from a linear pattern of reflection was used to detect eye saccades.
Figure 7B:
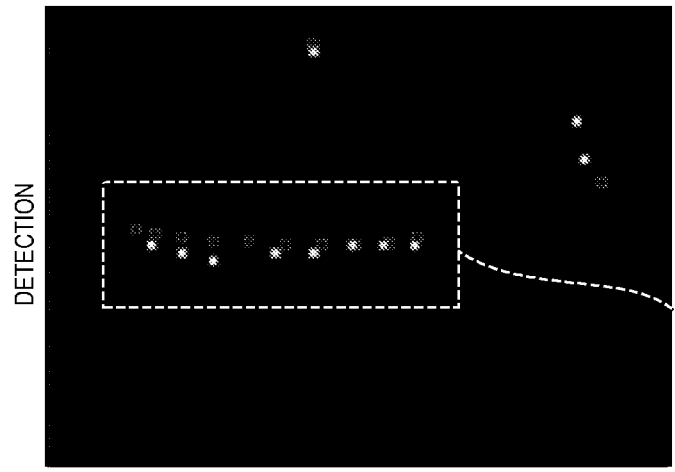
Figure 7A:
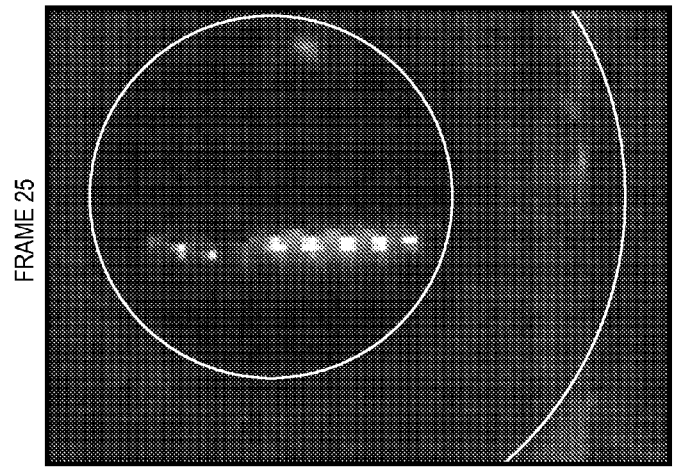

FIG. 7A, FIG. 7B, and FIG. 7C illustrate how the deviation from a linear pattern of reflection was used to detect eye saccades. FIG. 7A shows corneal reflection in the presence of inter-frame saccade. FIG. 7B and FIG. 7C show reflection location and offset indicating amount and timing of saccade. The dark pixel corresponded to sequence start. In this case, an inter-frame saccades began at $t_6$, or 0.04 seconds after frame 25 acquisition time.

Figure 8:
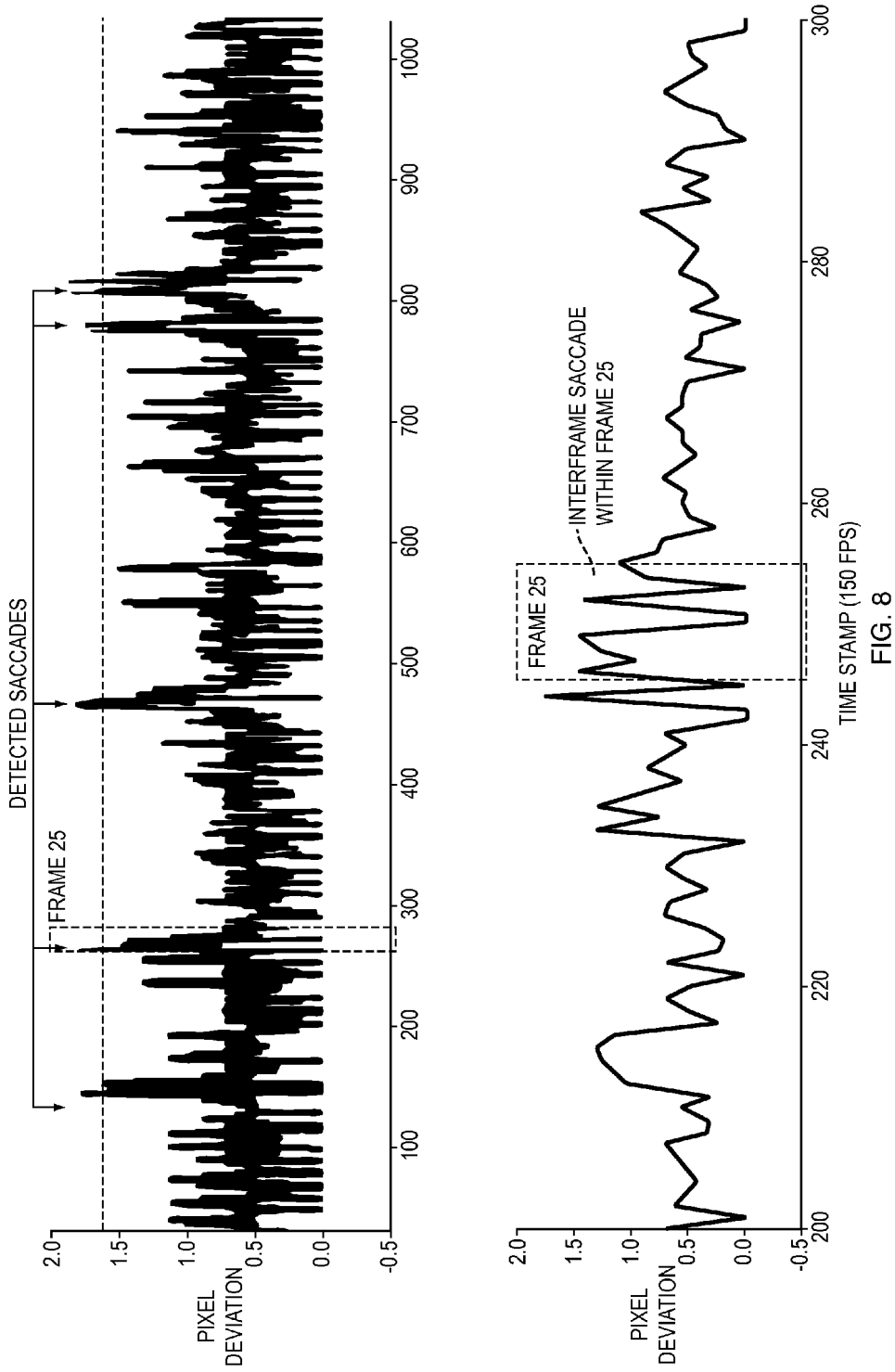
FIG. 8 is a plot showing the results of a saccade measurement using the methods and devices described herein. The plot is an image deviation from a reference position (in pixels) as a function of time.

FIGS. 7A through 7C demonstrate that the resultant deviation from the stationary reflectance pattern can be used to indicate inter-frame saccade time and amplitude during a single frame acquisition time at relatively low video sample rates. FIG. 8 shows an output saccade detection product. In FIG. 8, saccade detection at 150 fps was derived from 15 fps video. Note that in Frame 25 of FIG. 8, an interframe saccades has taken place.

Figure 9:
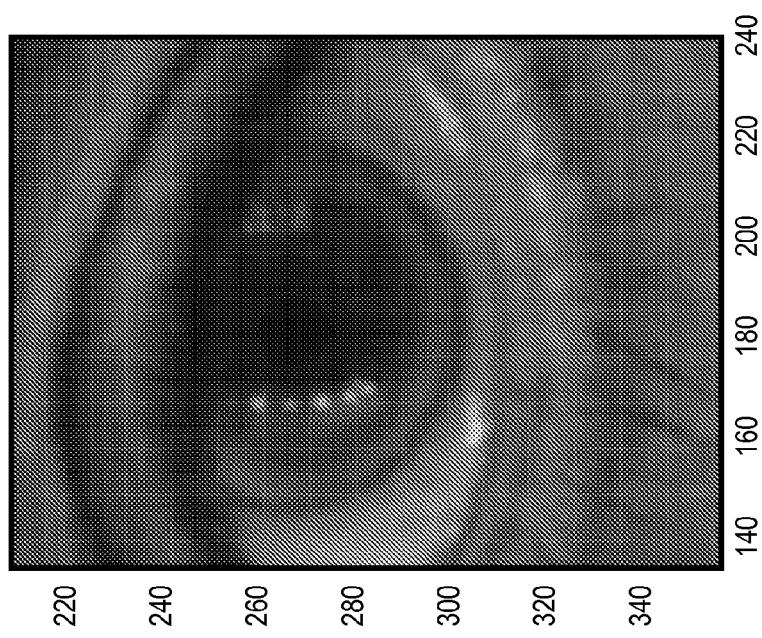
FIG. 9 is a photograph of the reflection of strobed light emitters from a human eye taken with hand-held iPhone 2.

Data collected with the iPhone2 using external line lighting indicates that there was sufficient resolution in mobile devices to be able to detect saccades effectively via the pixel deviation. As shown in FIG. 9, sample data was taken with a hand-held iPhone 2, which possessed sufficient resolution and contrast.

While this invention has been particularly shown and described with references to example embodiments thereof, it will be understood by those skilled in the art that various changes in form and details may be made therein without departing from the scope of the invention encompassed by the appended claims.

What is claimed is:

1. A device, comprising:
   a detector, configured to capture frames according to a frame acquisition time;
   a focusing element; and
   an illumination source configured, in cooperation with the focusing element and the detector, to generate at least first and second images of the illumination source on the detector within a given frame,
   the first image and the second images forming a spatial sequence and being spatially separated from each other on the focal plane of the detector by at least one pixel,
   the first and the second images being generated in a temporal sequence, the illumination source having a time delay between generating the first image and the second image, the time delay being less than or equal to the frame acquisition time of the detector.

2. The device of claim 1, further including a processing module configured to determine motion of the object based on the spatial sequence and the temporal sequence of the first image and the second image.

3. The device of claim 1, further including a transmitter configured to transmit at least the first and the second images to a remote storage site.

4. The device of claim 1, wherein the illumination source is located on the object.

5. The device of claim 1, wherein the illumination source is configured to emit electromagnetic energy at the object causing the electromagnetic energy to reflect, refract or diffract from the object to the detector.

6. The device of claim 5, wherein the detector, the focusing element, and the illumination source are integrated in a hand-held device.

7. The device of claim 1, wherein the illumination source is further configured, in cooperation with the focusing element and the detector, to generate a third image of the illumination source on the detector within the given frame, the first image, the second image, and the third image each being spatially separated from each other on the focal plane of the detector by at least one pixel,
   the illumination source having a first time delay between generating the first image and the second image, and a second time delay between generating the second image and the third image, wherein the first time delay and the second time delay are each less than or equal to the frame acquisition time of the detector.

8. The device of claim 1, wherein the illumination source includes at least two light emitters.

9. The device of claim 8, wherein the illumination source includes an array of sequentially activated light emitters.

10. The device of claim 9, wherein the light emitters are activated in a sequence that is free-running, synchronous, or plesiochrnoous with respect to the detector.

11. The device of claim 1, wherein the illumination source includes a single spatially modulated light emitter.

12. The device of claim 11, wherein the focusing element is an optical component within an optical train, and wherein the light emitter is spatially modulated by the optical train.

13. The device of claim 11, wherein the light emitter is movable.

14. A method of detecting relative motion of an object and an illumination source, the method comprising:
assigning a position tag and a time tag to representations of each of at least three spatially distinct images of the illumination source captured in a spatial sequence and a temporal sequence in a single frame of a detector;
comparing corresponding position tags and the time tags to each other and to reference position tags and reference time tags; and
detecting relative motion of the object and the illumination source based on the comparing.

15. The method of claim 14, wherein the illumination source is located on the object.

16. The method of claim 14, wherein the illumination source is configured to emit electromagnetic radiation at the object, causing the electromagnetic radiation to reflect, refract or diffract from the object.

17. The method of claim 14, wherein the reference position tags and the reference time tags are based on prior knowledge of the positional sequence and the temporal sequence of the at least three images.

18. The method of claim 14, wherein the reference position tags and the reference time tags are the position tags and time tags assigned to at least three images of the illumination source captured in a second frame.

19. The method of claim 14, further including determining relative motion of at least one additional object and the illumination source.

20. The method of claim 14, further including computing the object's position as a function of time and the object's velocity as the function of time.

21. The method of claim 14, further including computing the object's angular velocity.

22. A method of detecting saccades in a subject, the method comprising:
generating at least a first image and a second image of a reflection of an illumination source in at least one eye of the subject by the illumination source in cooperation with a focusing element, the first and second images generated in a temporal sequence;
detecting by a detector the first and second images, the first and second images being detected within a given frame, the first and second images being disposed on the focal plane of the detector in a spatial sequence; and
determining the motion of the at least one eye based on the spatial sequence and the temporal sequence of the first image and the second image,
the detector having a frame acquisition time, the illumination source having a time delay between generating the first image and the second image, the first image and the second image being spatially separated from each other on the focal plane of the detector by at least one pixel,
wherein the time delay of the illuminating source is less than or equal to the frame acquisition time of the detector.

23. The method of claim 22, wherein detecting the saccades includes detecting saccades along at least two axes.

24. The method of claim 22, further including distinguishing large saccades from small saccades.

25. The method of claim 22, further including saccades magnitude and saccades duration.

26. A method of detecting saccades in a subject, the method comprising:
assigning a position tag and a time tag to representations of each of at least three spatially distinct images of a reflection of an illumination source from an eye of the subject captured in a spatial sequence and a temporal sequence in a single frame of a detector;
comparing the corresponding position tags and time tags to each other and to reference position tags and reference time tags; and
detecting saccades in the subject based on the comparing.

27. The method of claim 26, wherein detecting the saccades includes detecting saccades along at least two axes.

28. The method of claim 26, further including distinguishing large saccades from small saccades.

* * * * *